US011452591B2

(12) United States Patent
Lim (10) Patent No.: US 11,452,591 B2
(45) Date of Patent: Sep. 27, 2022

(54) ARTIFICIAL HAIR IMPLANT DEVICE

(71) Applicant: HUMAN WELLNESS INC, Seoul (KR)

(72) Inventor: Sin Young Lim, Seoul (KR)

(73) Assignee: HUMAN WELLNESS INC, Seoul (KR)

( * ) Notice: Subject to any disclaimer, the term of this patent is extended or adjusted under 35 U.S.C. 154(b) by 249 days.

(21) Appl. No.: 16/623,455

(22) PCT Filed: Jun. 21, 2018

(86) PCT No.: PCT/KR2018/006999
§ 371 (c)(1),
(2) Date: Dec. 17, 2019

(87) PCT Pub. No.: WO2019/088392
PCT Pub. Date: May 9, 2019

(65) Prior Publication Data
US 2020/0253716 A1    Aug. 13, 2020

(30) Foreign Application Priority Data
Nov. 1, 2017  (KR) .......................... 10-2017-0144416

(51) Int. Cl.
*A61F 2/10* (2006.01)
*A61B 17/34* (2006.01)
(Continued)

(52) U.S. Cl.
CPC ............ *A61F 2/10* (2013.01); *A61B 17/3468* (2013.01); *A61F 2/0095* (2013.01);
(Continued)

(58) Field of Classification Search
CPC ...... A61F 2/10; A61F 2/0095; A61B 17/3468; A61B 2017/00367; A61B 2017/00477; A61B 2017/00752
(Continued)

(56) References Cited

U.S. PATENT DOCUMENTS 10,881,431 B2 *  1/2021  Suh ........................... A61F 2/10
2008/0033455 A1  2/2008  Rassman
(Continued)

FOREIGN PATENT DOCUMENTS

JP         2013013668 A     1/2013
KR    1020030040943 A     5/2003
(Continued)

OTHER PUBLICATIONS

Incoming Written Opinion 237 English translation; PCT/KR2018/006999 dated 2019.*

*Primary Examiner* — Suzette J Gherbi
(74) *Attorney, Agent, or Firm* — Patent Office of Dr. Chung Park (57) ABSTRACT

An artificial hair implant device is disclosed. The artificial hair implant device according to the present invention has: a body part having a hollow body; a head part in which a head is coupled and fixed to the body, an implant needle is provided to be able to enter and exit the head and has an artificial hair fitted around an end portion thereof that is drawn out from the head, and a return spring is provided between the implant needle and the head and returns the implant needle drawn out from the head back to an original position; and a button part in which a button is movably provided on the body, and a pressing shaft is provided under the button and enters and exits the body, thereby pressing the implant needle, such that the implant needle is drawn out from the head.

3 Claims, 9 Drawing Sheets

(51) Int. Cl.
*A61F 2/00* (2006.01)
*A61B 17/00* (2006.01)

(52) U.S. Cl.
CPC .............. *A61B 2017/00367* (2013.01); *A61B 2017/00477* (2013.01); *A61B 2017/00752* (2013.01)

(58) Field of Classification Search
USPC ............................................ 623/15.11–15.12
See application file for complete search history.

(56) References Cited

U.S. PATENT DOCUMENTS

| | | | |
|---|---|---|---|
| 2016/0120574 A1* | 5/2016 | Shiao | A61F 2/10 606/187 |
| 2017/0020564 A1* | 1/2017 | Bae | A61B 17/3468 |
| 2018/0153540 A1* | 6/2018 | Dolan | A61B 17/06109 |
| 2018/0325544 A1* | 11/2018 | Park | A61B 17/32053 |
| 2019/0053827 A1* | 2/2019 | Suh | A61M 5/3234 |
| 2019/0247089 A1* | 8/2019 | Lin | A61B 17/3205 |
| 2020/0046399 A1* | 2/2020 | Park | A61B 17/3468 |
| 2021/0077148 A1* | 3/2021 | Kim | A61B 17/3468 |
| 2021/0145476 A1* | 5/2021 | Franco | A61B 17/32053 |
| 2021/0228230 A1* | 7/2021 | Bloch | A61B 17/3403 |
| 2021/0282486 A1* | 9/2021 | Lim | A61L 27/18 |
| 2021/0315610 A1* | 10/2021 | Boudjema | A61B 17/3468 |

FOREIGN PATENT DOCUMENTS

| | | |
|---|---|---|
| KR | 10-0406160 | 11/2003 |
| KR | 1020120098780 A | 9/2012 |
| KR | 1020160020796 A | 2/2016 |

\* cited by examiner

ARTIFICIAL HAIR IMPLANT DEVICE

CROSS-REFERENCE TO RELATED APPLICATIONS

This application is a national stage application of International Patent Application No. PCT/KR2018/006999 filed on Jun. 21, 2018, which claims priority to Korean Patent Application No. 10-2017-0144416 filed on Nov. 1, 2017, the entire contents of which are incorporated by reference herein.

TECHNICAL FIELD

The present invention relates to an artificial hair implant device, and more particularly, to an artificial hair implant device for implanting artificial hair in the scalp.

BACKGROUND

Alopecia is a condition that may affect the personal appearance and eventually cause psychological distress.

It is known that baldness or alopecia is more prevalent in men than women, and about 70% of men and about 25% of women suffer from alopecia.

Although the causes are not yet clear, genetic factors are known to be the main causes, and also, endocrine disorders, autonomic nervous system abnormalities, allergies, hair root malnutrition, bacterial infections, aging, etc. are presumed to be the causes.

Recently, due to environmental factors such as air pollution, mental stress, and excessive use of hair beauty products such as spray and wax, the incidence of alopecia, a sort of baldness, is increasing, and the age of patients is gradually decreasing.

It is desirable that baldness or alopecia be cured and prevented in the early stages of development. However, when baldness or alopecia has been advanced too far, a wig proposed in Korean Patent No. 10-1129313 (title: a manufacturing method of wig and a wig using the same, hereinafter referred to as 'prior art document 1') may be used for a user who suffers from baldness or alopecia.

However, this wig is not only unnatural to wear, but also has the hassle and inconvenience of wearing and taking off.

Accordingly, in order to overcome the inconvenience of wigs, Korean Patent No. 10-0406160 (title: hair implanting system, hereinafter referred to as 'prior art document 2') has been proposed and is being used as proposed.

However, the hair implanting system disclosed in the prior art document 2 can automate the process of cutting hair roots and transplanting the hair roots to the affected area, but the hair implanting system according to the automation of hair implant is too large and complicated. Accordingly, it is difficult to generalize the hair implant, and the cost for hair implant is high.

SUMMARY

Accordingly, the present invention provides an artificial hair implant device which can quickly and easily implant artificial hairs on the scalp by simplifying and miniaturizing the structure of the implant device for implanting artificial hairs on the scalp.

In one general aspect, an artificial hair implant device for implanting an artificial hair in a scalp includes: a body part having a hollow body; a head part including a head coupled and fixed to the body, an implant needle provided to enter and exit the head while the artificial hair is fitted on an end portion drawn from the head, and a return spring disposed between the implant needle and the head to return the implant needle drawn from the head to the original position; and a button part movably provided in the body and a push shaft pressing the implant needle to draw out from the head while entering and exiting the body, wherein the head has an end portion thereof making contact with the scalp and having an inclined surface, and the implant needle entering and exiting the inclined surface of the head is drawn while being biased to a long end portion of the head.

The implant needle may have a hook formed at an end portion thereof entering and exiting the head, and a long end portion of the hook may be located at a short end portion of an inclined surface of the head.

The head may be provided with the implant needle inserted into the inside of the head and may be provided with a coupling pipe at the outside thereof while a return spring is fitted on the coupling pipe, and the implant needle may be provided with a coupling member which is coupled and fixed to one end portion of the implant needle and supported by the return spring.

The coupling member of the implant needle may be provided with a guide protrusion which outwardly protrudes and makes contact with the return spring during movement, and the coupling pipe may be provided with a guide groove which is formed at a location corresponding to the guide protrusion and guides the guide protrusion that is inserted therein while preventing the rotation of the implant needle.

Other features and aspects will be apparent from the following detailed description, the drawings, and the claims.

According to an artificial hair implant device of the present invention, the implant device for implanting artificial hair into the scalp includes a body part, a button part and a head part and is miniaturized such that an operator can hold the implant device in hand, thereby allowing the artificial hair to be quickly and easily implanted and allowing the artificial hair to be accurately implanted into the hairy fascia in the scalp.

DETAILED DESCRIPTION OF THE DISCLOSURE

Hereinafter, exemplary embodiments of the present invention will be described in detail with reference to the accompanying drawings.

Terms used in the present disclosure are terms defined in consideration of functions in the present disclosure, which may vary according to a user's intention or an operator's intention or custom, and thus, definitions of these terms are intended to be consistent with the technical matters of the present disclosure.

In particular, the term "and/or" used in the present disclosure is used in the meaning including at least one or more of the components listed before and after, and "one or more" means one or plurality of two or more.

In addition, optional terms such as "first", "second", "one side", and "other side" used in the present disclosure are used to distinguish one component from another component, and the component is not limited by the terms described above.

In the present disclosure, "formed on" and "formed on the side surface" do not mean only that the components are directly stacked in contact with each other, but also mean that other components are further formed between the corresponding components. For example, "formed on" means that the second component is formed in direct contact with the first component and the third component is further formed between the first component and the second component.

FIGS. 1 to 9 are views illustrating an artificial hair implant device and components thereof according to an embodiment of the present invention.

As shown in FIGS. 1 to 4, an artificial hair implant device 100 according to an embodiment of the present invention is a device which has a shape of a pen to implant an artificial hair 500 into the scalp.

Figure 1:
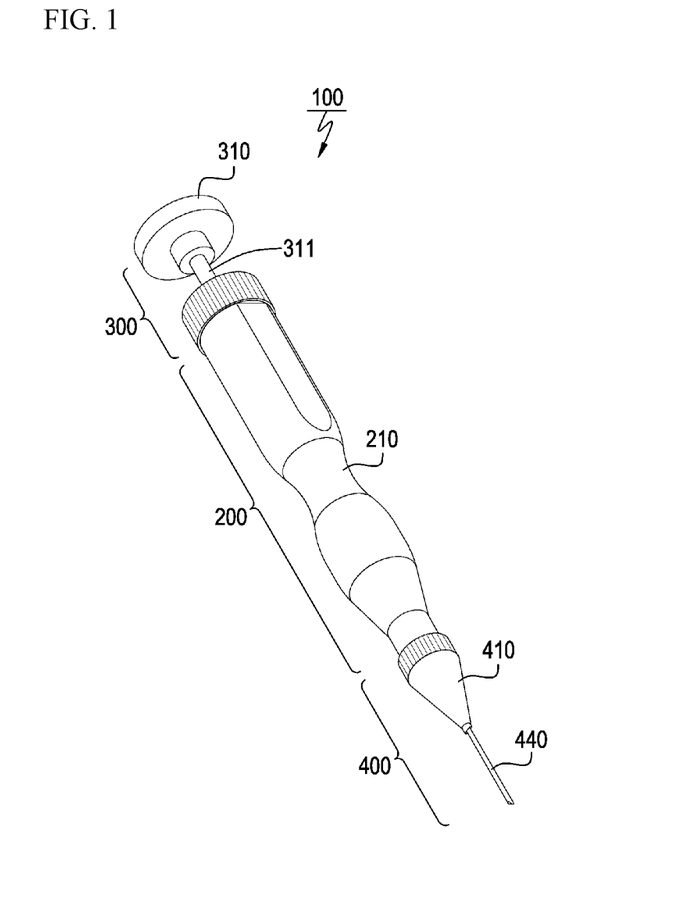
FIG. 1 is a view illustrating a coupling configuration of an artificial hair implant device according to an embodiment of the present invention.
Figure 3:
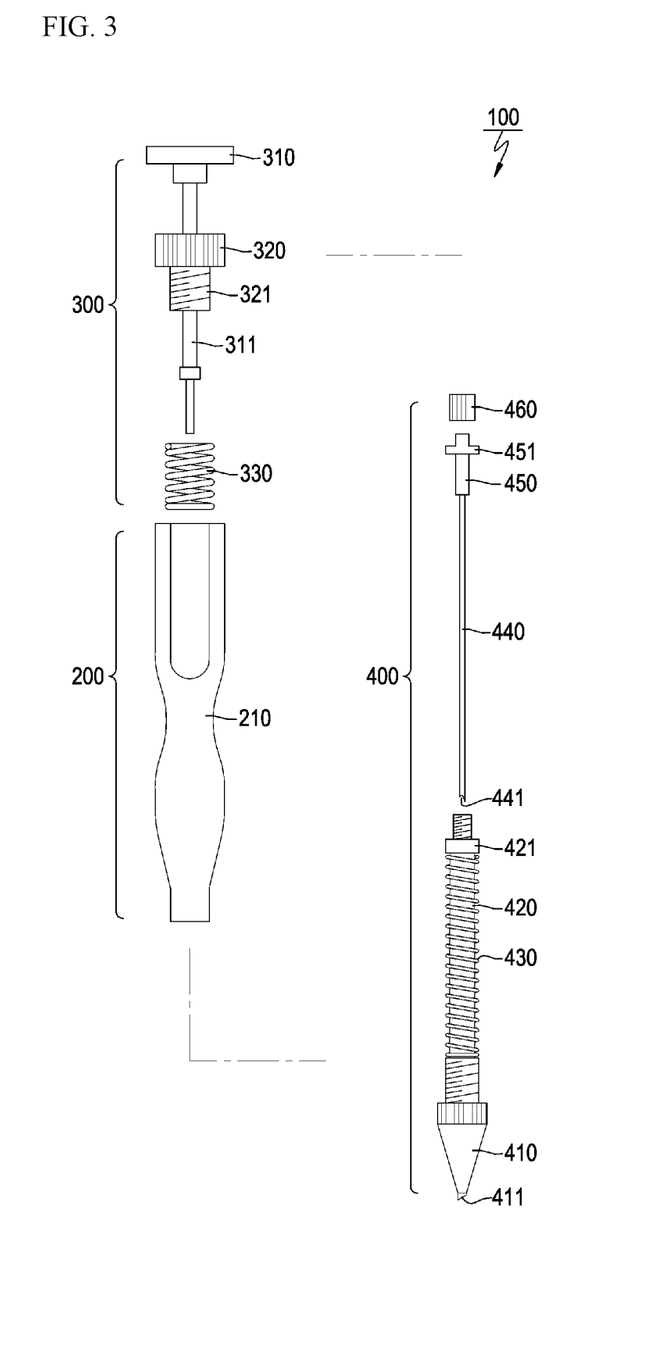
FIG. 3 is an exploded view illustrating components of an artificial hair implant device according to an embodiment of the present invention.

As shown in FIGS. 1 and 3, the implant device 100 may include a body part 200, a head part 400 disposed at the front end of the body part 200, and a button part disposed at the rear end of the body part 200.

First, the body part 200 includes a hollow body 210, and the hollow body 210 is formed such that both ends, i.e., the front end and the rear end thereof are opened in communication with each other.

The body 210 is a part of the implant device 100 which a user grips by hand when the artificial hair 500 is implanted, and is formed to have a certain length such that there is no inconvenience in gripping the implant device 100.

Figure 4:
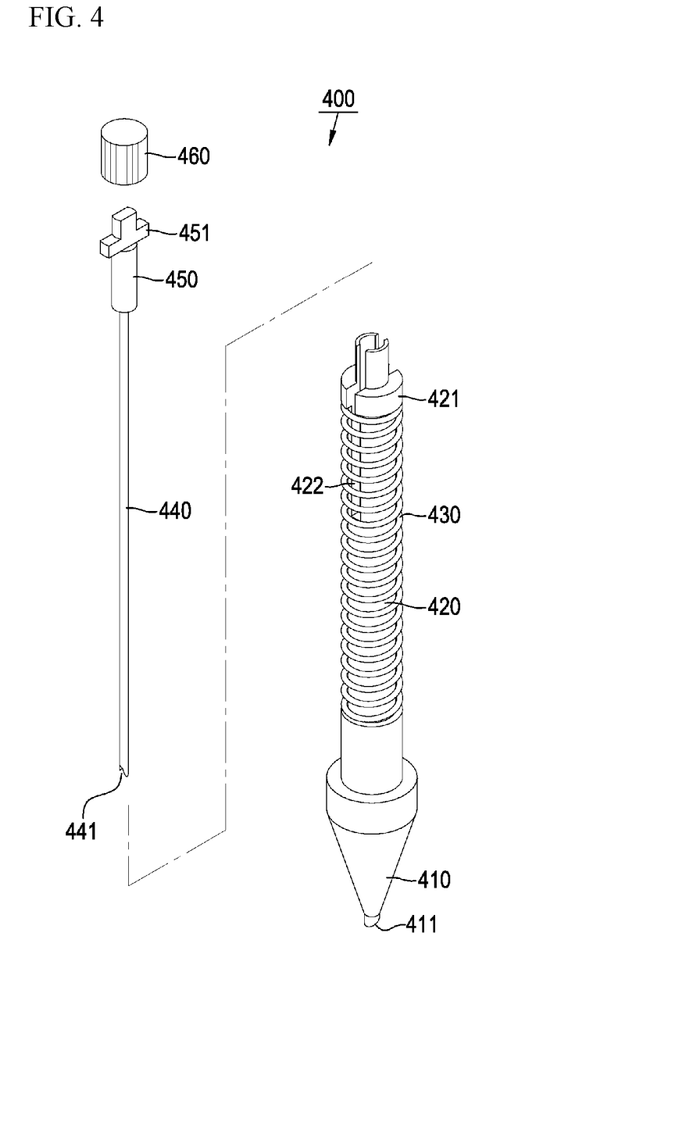
FIG. 4 is an exploded view illustrating a head and an implant needle of an implant device according to an embodiment of the present invention.

As shown in FIGS. 3 and 4, the head part 400 is disposed at the front end of the body 210. That is, the head part 400 includes a head 410 fixedly coupled to the front end of the body 210, an implant needle 440 withdrawably disposed at the front end of the head 410, and a first return spring 430 disposed between the implant needle 440 and the head 410 to return the implant needle 440 withdrawn from the head 410 to the original position.

The head 410 is formed to have an inclined surface 411 such that the front end thereof is inclined in an oblique direction, and the rear end of the head 410 is detachably screwed to the front end of the body 210.

In particular, the inclined surface of the head 410 is formed to be inclined at an angle of about 45 degrees, and a long end portion 411a and a short end portion 411b are formed at both sides of the inclined surface 411.

Figure 8:
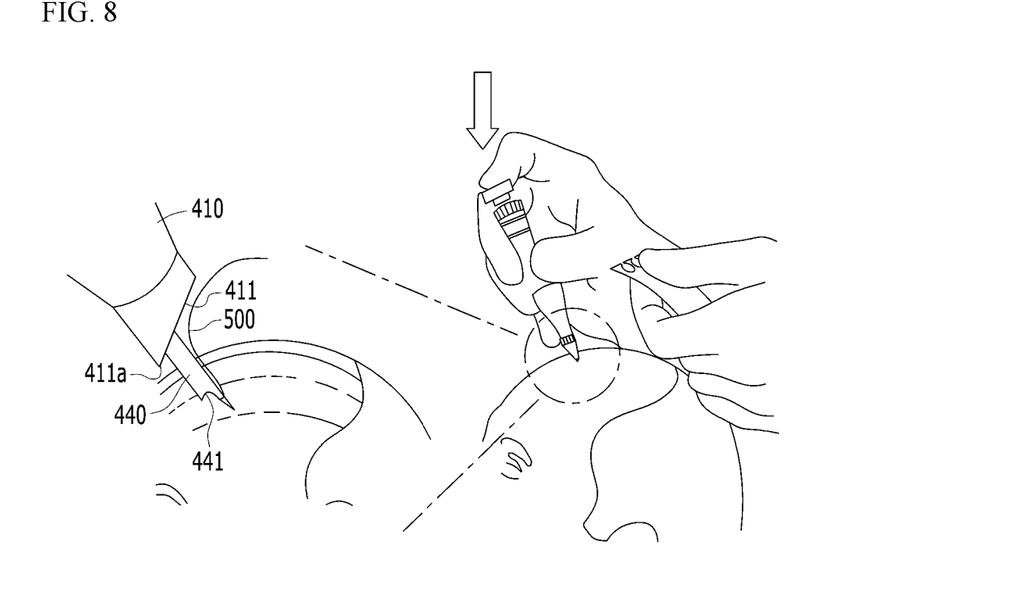
FIG. 8 is a view illustrating a state in which an artificial hair is implanted on the scalp using an implant device according to an embodiment of the present invention.

The inclined surface 411 of the head 410 secures a minimum discrimination space that enables a user to determine the state of the implant needle 440 withdrawn from the head 410 when implanting the artificial hair 500 in the scalp. That is, as shown in FIG. 8, when the artificial hair 500 is implanted, the implant device 100 is inclined to the scalp side while the long end portion 411a of the head 410 is in contact with the scalp, allowing an angle between the short end portion 411b and the scalp to be an obtuse angle. Thus, it is possible to easily determine whether or not the artificial hair 500 and the implant needle 440 withdrawn from the head 410 maintain proper positions.

In addition, a boss for screw-coupling to the body 210 may protrude from the rear end of the head 410, and a coupling pipe 420 may be integrally formed with the boss, or may be inserted into and fixed in the boss.

The coupling pipe 420 is formed of a hollow member, and a flange 421 is formed to protrude from a rear end portion of the coupling pipe 420 in a direction perpendicular to the axial direction.

A guide groove 422 is formed at the rear end portion of the coupling pipe 420. The guide groove 422 receives and guides a guide protrusion 451 of a coupling member 450 to be described later, which is coupled to the implant needle 440. The guide groove 422 is longitudinally formed along the axial direction from the rear end of the coupling pipe 420 toward the front end of the coupling pipe 420.

On the other hand, a first return spring 430, which is the compression coil spring, is provided on the outer circumferential surface of the coupling pipe 420. The first return spring 430 is provided such that both ends thereof make contact with the rear surface of the head 410 and the flange 421 of the coupling pipe 420. In this case, when the implant needle 440 moves, the first return spring 430 is compressed to the head 410 by the guide protrusion 451 of the coupling member 450 provided on the implant needle 440.

In addition, the implant needle 440 is a needle that enters and exits the head 410 while being inserted into the coupling pipe 420 of the head 410. Also, a hook 441 is formed at a front end of the implant needle 440, and a long end portion 441a and a short end portion 441b are formed at both sides of the hook 441.

The hook 441 of the implant needle 440 formed as described above is provided so as to enter and exit the inclined surface 411 of the head 410. In this case, the hook 441 of the implant needle 440 is provided so as to be withdrawn while being biased toward the long end portion 411a of the head 410. To this end, a hole from which the implant needle 440 is withdrawn may be formed on the inclined surface 411 of the head 410 so as to be biased toward the long end portion 411a of the inclined surface 411.

Figure 2:
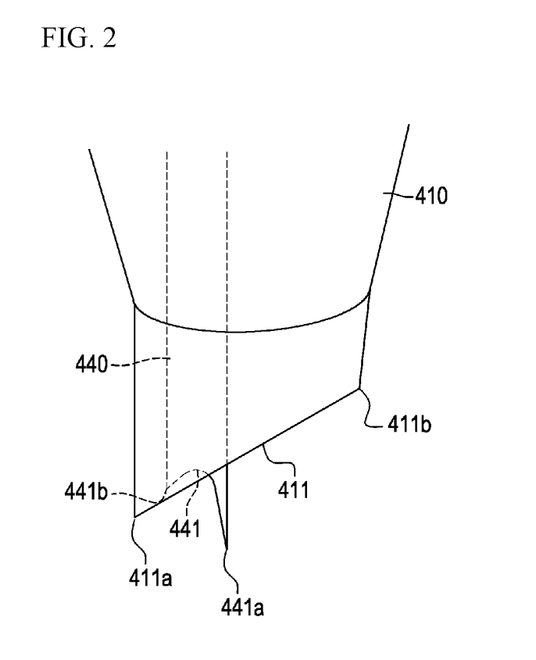
FIG. 2 is an enlarged view illustrating a head end portion of an implant device according to an embodiment of the present invention.

In addition, the hook 441 of the implant needle 440 is provided such that the long end portion 441a is located at the side of the short end portion 411b of the inclined surface 411 of the head 410. This is to maximally secure the length of the long end portion 441a of the hook 441 protruding from the end of the head 410 when the implant needle 440 is inserted into the head 410 before the operation of the implant needle 440 as shown in FIG. 2.

Figure 6:
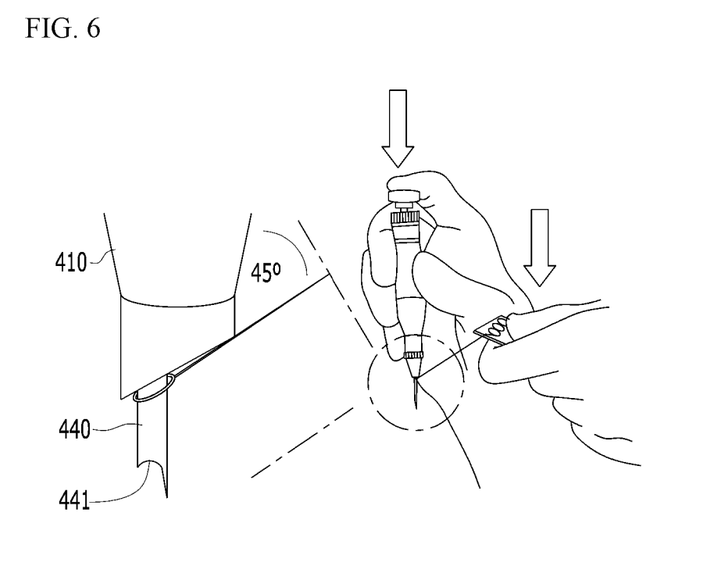
FIG. 6 is a view illustrating a state in which an artificial hair is fitted on an implant needle of an implant device according to an embodiment of the present invention.
Figure 7:
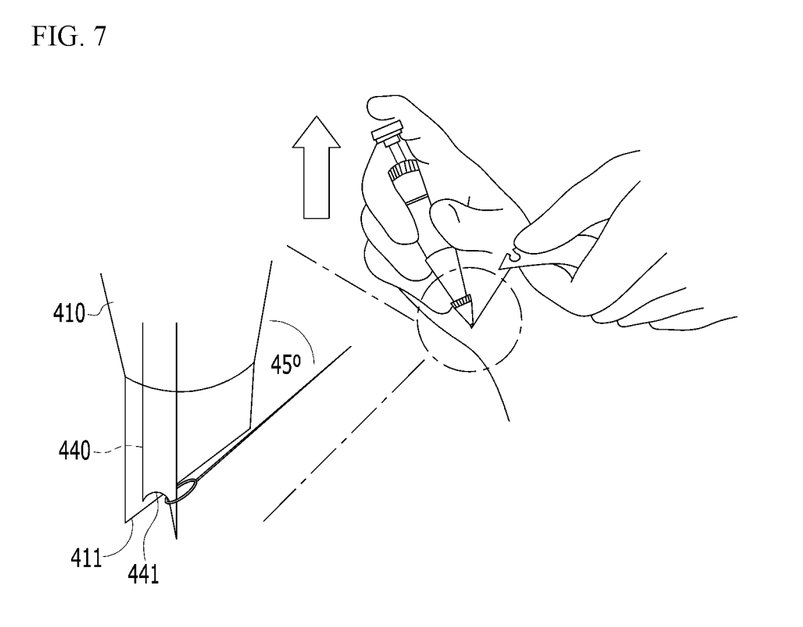
FIG. 7 is a view illustrating a state in which an implant needle of an implant device combined with an artificial hair is returned to its original position according to an embodiment of the present invention.

That is, in order to fit the artificial hair 500 on the implant needle 440, as shown in FIG. 6, the implant needle 440 is withdrawn from the head 410 to penetrate the ring portion 510 of the artificial hair 500. Thereafter, the artificial hair 500 is pulled and caught on the implant needle 440 while being in close contact with the inclined surface 411 of the head 410. Although the implant needle 440 provided with the artificial hair 500 is again inserted into the head 410 and is returned to its original position, the long end portion 441a of the hook 441 sufficiently protrudes from the inclined surface 411 of the head 410 even at the original position of the implant needle 440. Accordingly, as shown in FIG. 7, the artificial hair 500 is provided in close contact with the inclined surface 411 of the head 410, and then returns to the original position, thereby being easily caught on the long end portion 441a of the hook 441 protruding from the end portion of the head 410. However, when the hook 441 of the implant needle 440 is positioned in the opposite direction to the direction described above, that is, when the long end portion 441a of the hook 441 is located at the side of the long end portion 411a of the inclined surface 411, the artificial hair 500 cannot be caught on the hook 441 during the above-described operation because the length of the long end portion 441a of the hook 441 outwardly protruding from the head 410 in the original state in which the implant needle 440 is inserted into the head 410 is short.

Also, a coupling member 450 that is fixed to the implant needle 440 is provided at the rear end of the implant needle 440. The coupling member 450 includes guide protrusions 451 vertically protruding at both sides thereof. The guide protrusion 451 moves up and down while being inserted into the guide groove 422 of the coupling pipe 420, thereby preventing the rotation of the implant needle 440 and allowing the long end portion 441a of the hook 441 to be correctly located at the side of the short end portion 411b side of the head 410 in spite of the repeated operation.

As described above, a first ring nut 460 is coupled to the rear end portion of the coupling pipe 420 into which the implant needle 440 is inserted, thereby blocking the end portion of the guide groove 422 and thus preventing the separation of the implant needle 440.

Meanwhile, the button part 300 is configured at the rear end of the body 210. As shown in FIG. 3, the button part 300 includes a button 310 movably inserted into the rear end of the body 210 and a push shaft 311 disposed at the front end of the button 310 and pushing and withdrawing the implant needle 440 from the head 410 while entering and exiting the body 210.

The button 310 is formed of a plate for easy pressing, and the push shaft 311 is formed to protrude toward the body 210. The push shaft 311 may be formed as one shaft penetrating through a second ring nut 320 coupled to the rear end of the body 210, or may be dividedly formed as two shafts based on the second ring nut 320. On the other hand, although not shown in the drawing, in the former case, a support protrusion which is supported in contact with a second return spring 330 may be formed on a shaft located under the second ring nut 320. In the latter case, the support protrusion as described above may be formed on a lower shaft located under the second ring nut 320. The support protrusion may be caught by the second ring nut 320 to prevent the button 310 from being separated.

The second ring nut 320 is screw-coupled to the rear end of the body 210, and a hollow coupling boss 321 that is screw-coupled to the body 210 protrudes from one surface of the second ring nut 320.

In addition, the second return spring 330 is provided in the body 210 under the second ring nut 320, and both ends of the second return spring 330 are respectively supported by the body 210 and the push shaft 311 of the button 310.

Accordingly, when the button 310 is operated, the second return spring 330 is compressed by the push shaft 311 drawn into the body 210, and the tensile force of the compressed second return spring 330 serves as a restoring force for returning the button 310 to the original position.

On the other hand, the push shaft 311 of the button 310 may be provided such that the lower end thereof inserted into the body 310 makes contact with the upper end of the coupling member 450 coupled to the implant needle 440.

Then, when the second ring nut 320 is coupled to or released from the body 210, the height of the button 310 coupled thereto, that is, the length of the push shaft 311 protruding from the body 210 can be adjusted. Accordingly, it is possible to adjust the length of the implant needle 440 withdrawn from the head 410.

Hereinafter, an operation relationship of the implant device and an implant process of artificial hair according to an embodiment of the present invention will be described.

Figure 5:
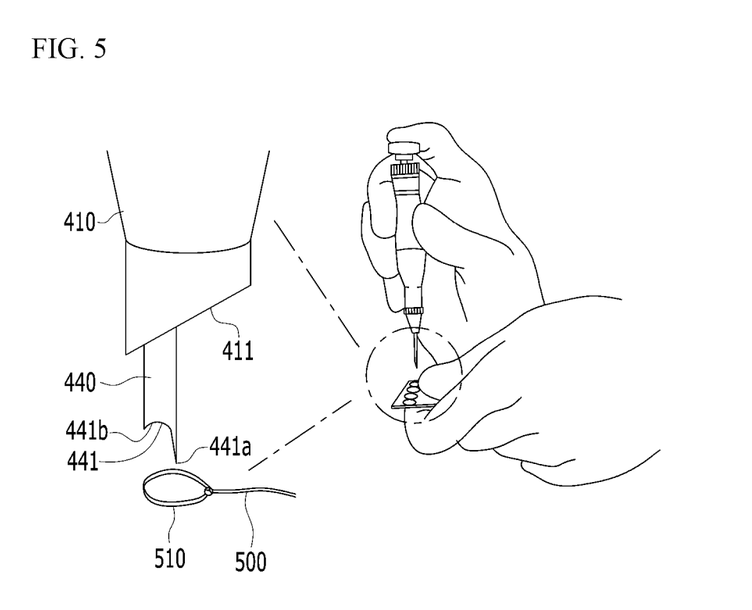
FIG. 5 is a view illustrating a process of fitting an artificial hair on an implant needle of an implant device according to an embodiment of the present invention.

First, as shown in FIG. 5, when the button 310 of the implant device 100 is pressed, the push shaft 311 descends together with the button 310 to be inserted into the body 210. The implant needle 440 is pressed by the push shaft 311 to descend in the coupling pipe 420 while the hook 441 of the implant needle 440 protrudes outward through the inclined surface 411 of the head 410.

In this case, the first and second return springs 430 and 330 are compressed by the implant needle 440 and the push shaft 311, respectively.

In this state, as shown in FIG. 6, the implant needle 440 withdrawn from the head 410 penetrates the ring portion 510 of the artificial hair 500, and then the artificial hair 500 is pulled to be coupled and fixed to the implant needle 440 while being in close contact with the inclined surface 411 of the head 410.

Then, as shown in FIG. 7, when an external force is removed from the button 310 that is pressed, the implant needle 440, the button 310, and the push shaft 311 ascend in the coupling pipe 420 and the body 210 by the tensile force of the first and second return springs 430 and 330 to return to the original positions, respectively.

In particular, as the implant needle 440 ascends into the coupling pipe 420 in the return process, the hook 441 withdrawn out of the head 410 is inserted into the head 410, but the long end portion 441a of the hook 441 is not completely inserted into the head 410. Since the long end portion 441a of the hook 441 protrudes from the head 410 by a certain length, the ring portion 510 of the artificial hair 500 is caught by the long end portion 441a of the hook 441 which is protruded.

After the implanting device 100 provided with the artificial hair 500 is brought to the target part, the implant device 100 is inclined while the long end portion 411a of the inclined surface 411 of the head 410 is in contact with the scalp as shown in FIG. 8. In a state where the short end portion 411b of the head 410 and the scalp are spread at an obtuse angle, the button 310 of the implanting device 100 is again pushed to withdraw the implant needle 440.

Then, the needle 440 that is withdrawn is inserted into the hairy fascia through the scalp, i.e., the epidermis, the dermis, and the subcutaneous tissue while the implant needle 440 is combined with the ring portion 510 of the artificial hair 500.

Figure 9:
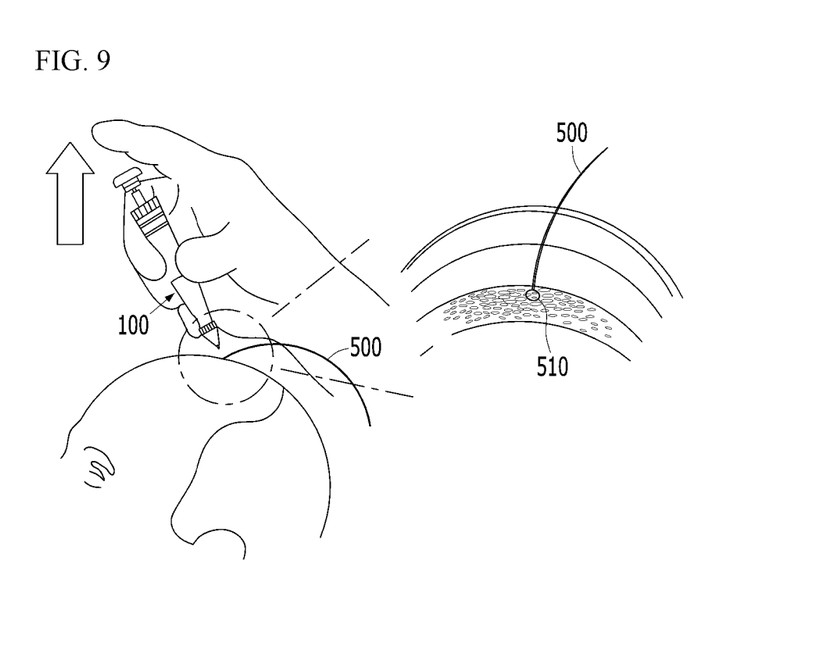
FIG. 9 is a view illustrating an artificial hair implanted using an implant device according to an embodiment of the present invention.

In this state, as shown in FIG. 9, when the implant needle 440 is returned to its original position by removing the external force pressing the button 310, the hook 441 of the implant needle 440 exits and returns from the hairy fascia. However, the ring portion 510 of the artificial hair 500 inserted into the hairy fascia is fixed and implanted in a state of being embedded in the hairy fascia.

Accordingly, the artificial hair 500 can be quickly and easily implanted into the scalp using the implant device 100 according to an embodiment of the present invention.

Although the present disclosure has been described in detail through specific examples, it is intended to describe the present disclosure in detail, and the present disclosure is not limited thereto. Also, it is obvious that modifications and improvements by those skilled in the art are possible within the technical spirit of the present disclosure.

Simple modifications and changes of the present disclosure all fall within the scope of the present disclosure, and the specific scope of protection of the present disclosure will be apparent from the appended claims.

What is claimed is:

1. An artificial hair implant device for implanting an artificial hair in a scalp, the device comprising:
    a body part having a hollow body;
    a head part comprising a head coupled and fixed to the body, an implant needle provided to enter and exit the head while the artificial hair is fitted on an end portion drawn from the head, and a return spring disposed between the implant needle and the head to return the implant needle drawn from the head to an original position; and
    a button part movably provided in the body and a push shaft pressing the implant needle to draw out from the head while entering and exiting the body,
    wherein the head has an end portion, the end portion of the head is configured to make a contact with a scalp and has an inclined surface, and the implant needle entering and exiting the inclined surface of the head is drawn while being biased to a long end portion of the head, and
    wherein the implant needle has a hook formed at an end portion thereof entering and exiting the head, and a long end portion of the hook is located at a short end portion of the inclined surface of the head.

2. An artificial hair implant device for implanting an artificial hair in a scalp, the device comprising:
    a body part having a hollow body;
    a head part comprising a head coupled and fixed to the body, an implant needle provided to enter and exit the head while the artificial hair is fitted on an end portion drawn from the head, and a return spring disposed between the implant needle and the head to return the implant needle drawn from the head to an original position; and
    a button part movably provided in the body and a push shaft pressing the implant needle to draw out from the head while entering and exiting the body,
    wherein the head has an end portion, the end portion of the head is configured to make a contact with a scalp and has an inclined surface, and the implant needle entering and exiting the inclined surface of the head is drawn while being biased to a long end portion of the head, and
    wherein the head is provided with the implant needle inserted into an inside of the head and is provided with a coupling pipe at an outside thereof while a return spring is fitted on the coupling pipe, and the implant needle is provided with a coupling member which is coupled and fixed to one end portion of the implant needle and supported by the return spring.

3. The artificial hair implant device of claim 2, wherein the coupling member of the implant needle is provided with a guide protrusion which outwardly protrudes and makes contact with the return spring during movement, and the coupling pipe is provided with a guide groove which is formed at a location corresponding to the guide protrusion and guides the guide protrusion that is inserted therein while preventing the rotation of the implant needle.

* * * * *